United States Patent [19]

Yoshio et al.

[11] Patent Number: 4,849,350
[45] Date of Patent: Jul. 18, 1989

[54] NOVEL DNA, PRODUCTION AND USE THEREOF

[75] Inventors: Taniyama Yoshio, Osaka; Igarashi Koichi, Kyoto; Marumoto Ryuji, Ashiya, all of Japan

[73] Assignee: Takeda Chemical Industries, Ltd., Osaka, Japan

[21] Appl. No.: 784,844

[22] Filed: Oct. 4, 1985

[30] Foreign Application Priority Data

Oct. 9, 1984 [JP] Japan .................................. 59-210502
Aug. 13, 1985 [JP] Japan .................................. 60-176976

[51] Int. Cl.⁴ ...................... C12P 21/00; C12P 19/34; C12N 15/00; C07H 15/12
[52] U.S. Cl. ........................................ 435/68; 435/70; 435/91; 435/235; 435/252.33; 435/172.3; 435/317.1; 435/320; 435/240.1; 935/11; 935/29; 935/34; 935/60; 536/27
[58] Field of Search ................. 435/68, 91, 172.3, 253, 435/317, 240; 536/27; 935/11, 29, 34, 60, 70, 72, 320, 317.1

[56] References Cited

FOREIGN PATENT DOCUMENTS 0046039 2/1982 European Pat. Off. .
PCT/US83/-
00650 5/1983 PCT Int'l Appl. .
04030 11/1988 World Int. Prop. O. .

OTHER PUBLICATIONS

Urdea et al. (1983), PNAS80:7461-5.
J. Smith et al., Nucleic Acids Research, 10, 4467-4482 (1982).
M. S. Urdea et al., Pro. Natl. Acad. Sci. U.S.A., 80, 7461-7465 (1983).

*Primary Examiner*—Thomas G. Wiseman
*Assistant Examiner*—S. Seidman
*Attorney, Agent, or Firm*—Ernest V. Linek; David G. Conlin

[57] ABSTRACT

The present invention presents a DNA containing a synthetic gene for expression of human epidermal cell growth factor of the DNA sequence;

AACAGTGATTCAGAATGTCCTCTCTCACACGATGGAT
ACTGCCTCCATGACGGCGTGTGTATGTATATTGAAGC
ACTAGACAAATACGCATGCAACTGTGTAGTTGGCTAT
ATTGGTGAACGATGCCAGTACCGAGATCTGAAATGGT
GGGAACTGCGA.

The adoption of the DNA of the present invention improves the stability of mRNA, the translation efficiency and the influence of the high-dimensional structure which is determined by the mRNA sequence, and made it possible to produce hEGF efficiently.

19 Claims, 8 Drawing Sheets

Figure 1

```
    1               5                   10                  15
AsnSerAspSerGluCysProLeuSerHisAspGlyTyrCysLeuHis
AACAGTGATTCAGAATGTCCTCTCTCACACGATGGATACTGCCTCCAT 20                  25                  30
AspGlyValCysMetTyrIleGluAlaLeuAspLysTyrAlaCysAsn
GACGGCGTGTGTATGTATATTGAAGCACTAGACAAATACGCATGCAAC 35                  40                  45
CysValValGlyTyrIleGlyGluArgCysGlnTyrArgAspLeuLys
TGTGTAGTTGGCTATATTGGTGAACGATGCCAGTACCGAGATCTGAAA

50
TrpTrpGluLeuArg
TGGTGGGAACTGCGA
```

Figure 2

```
              1               5              10             15
Eco RI    MetAsnSerAspSerGluCysProLeuSerHisAspGlyTyrCysLeuHis
5'  AATTCTATGAACAGTGATTCAGAATGTCCTCTCTCACACGATGGATACTGCCTCCAT
3'      GATACTTGTCACTAAGTCTTACAGGAGAGAGTGTGCTACCTATGACGGAGGTA 20              25             30
    AspGlyValCysMetTryIleGluAlaLeuAspLysTyrAlaCysAsnCysValVal
5'  GACGGCGTGTGTATGTATATTGAAGCACTAGACAAATACGCATGCAACTGTGTAGTT
3'  CTGCCGCACACATACATATAACTTCGTGATCTGTTTATGCGTACGTTGACACATCAA 40              45             50
    GlyTyrIleGlyGluArgCysGlnTyrArgAspLeuLysTrpTrpGluLeuArgTer
5'  GGCTATATTGGTGAACGATGCCAGTACCGAGATCTGAAATGGTGGGAACTGCGATAG
3'  CCGATATAACCACTTGCTACGGTCATGGCTCTAGACTTTACCACCCTTGACGCTATC
                                    -------
                                     BglII

5'  CTGCAGAG            Bam HI
3'  GACGTCTCCTAG
    ------
     Pst I
```

Figure 3

| | |
|---|---|
| #1 | A A T T C T A T G A A C A G T |
| #2 | G A A T C A C T G T T C A T A G |
| #3 | G A T T C A G A A T G T C C T C T |
| #4 | G T G A G A G A G G A C A T T C T |
| #5 | C T C A C A C G A T G G A T A C T |
| #6 | G A G G C A G T A T C C A T C G T |
| #7 | G C C T C C A T G A C G G C G T G |
| #8 | A T A C A C G C C G T C A T G |
| #9 | T G T A T G T A T A T T G A A G C |
| #10 | C T A G T G C T T C A A T A T A C |
| #11 | A C T A G A C A A A T A C G C A T |
| #12 | A G T T G C A T G C G T A T T T G T |
| #13 | G C A A C T G T G T A G T T G G C |
| #14 | A A T A T A G C C A A C T A C A C |
| #15 | T A T A T T G G T G A A C G A T G |
| #16 | T A C T G G C A T C G T T C A C C |
| #17 | C C A G T A C C G A G A T C T G |
| #18 | C A T T T C A G A T C T C G G |
| #19 | A A A T G G T G G G A A C |
| #20 | A T C G C A G T T C C C A C |
| #21 | T G C G A T A G C T G C A G A G |
| #22 | G A T C C T C T G C A G C T |

NOVEL DNA, PRODUCTION AND USE THEREOF

FIELD OF THE INVENTION

This invention relates to recombinant DNA techniques useful for the production of human epidermal cell growth factor (abbreviated hereinafter 'hEGF'). The present invention particularly relates to a synthetic gene corresponding to hEGF, to DNA containing this gene, to a host organism transformed by this DNA and to a method for producing hEGF.

BACKGROUND OF THE INVENTION hEGF is a polypeptide hormone consisting of 53 amino acids secreted mainly from the duodenum and sub maxillary glands. hEGF is capable of restraining gastric acid secretion and expediting the growth of epidermal cells. The hEGF function in restraining gastric acid indicates its possible use as a medicine for treating duodenal ulcers. Besides, hEGF is known to cause various biological reactions as a result of its combination with the EGF receptor located at the membranous surface of cells [D. Gospodarowicz, Ann. Rev. Physiol., 43, 251 (1981)]. Reaction caused by EGF is identical to that caused by the product of oncogene of tumor virus. It is therefore interesting from the view point of searching for the mechanism of carcinogenesis to elucidate the role of EGF in vivo and the mechanism of developing and controlling cells. However, since natural hEGF exists in extremely small in quantities, the production of hEGF by means of recombinant DNA has begun to attract a great deal of attention. Obtaining the hEGF gene from human tissues is difficult due to the presence of numerous restriction sites. In fact, the DNA sequence of hEGF has not yet been determined.

One example for the expression of a chemically synthesized structural gene based on the known amino acid sequence of hEGF has been reported [H. Gregory, Nature, 257, 325 (1975)]. However, the EGF is expressed only as a fusion peptide, and considering that it is a comparatively low molecular weight peptide, it is recognized as a foreign substance in a bacteria and easily digested with enzyme [J. Smith et al., Nucleic Acids Research, 10, 4467 (1982)]. A method of removing unnecessary parts from the fusion peptide has been proposed, but it is extremely uncertain (Stephen James Bruer et al., EP Patent Provisional Publication No. 89 626). An example of direct expression of the hEGF gene itself was conducted in yeast [M. S. Urdea et al., Proc. Natl. Acad. Sci. U.S.A., 80, 7461 (1983)]. The quantity of the expression was so little, and coupled with the slow yeast growth, the method is not adequate for quantity production.

SUMMARY OF THE INVENTION

As mentioned above, the DNA sequence of hEGF gene has not yet been determined. Previous attempts to express a synthetic gene based on the amino acid sequence of hEGF have not been successful. Such gene expression as a fusion peptide is accompanied with the complication of its manipulation and the difficulty of removing unnecessary parts from the peptide. When the above mentioned synthetic gene was directly expressed without being altered to a fusion peptide, the method was not practical because the yield was extremely low.

The present invention overcomes these difficulties by providing an efficient method for producing hEGF. The present inventors have created a synthetic DNA sequence for hEGF adequate for this purpose and established a method of producing this synthetic gene, a recombinant DNA containing this gene, a host organism transformed with the recombinant DNA and a method of producing hEGF thereby.

A BRIEF DESCRIPTION OF DRAWINGS

FIG. 1 shows the DNA sequence of the synthetic gene of the present invention and the sequence of amino acids corresponding to hEGF.

FIG. 2 shows an example of split for DNA fragments when hEGF genes of the present invention are synthesized.

FIG. 3 shows an example of DNA fragments for manufacturing the synthetic hEGF genes of the present invention.

DESCRIPTION OF THE INVENTION

Figure 4:
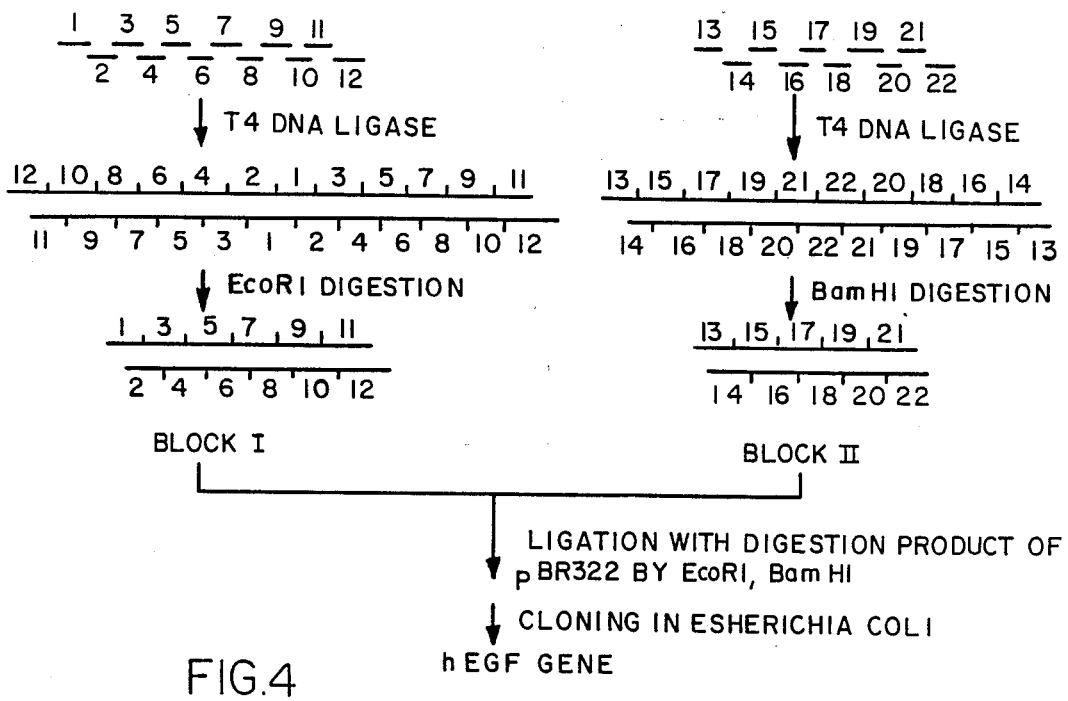
FIG. 4 shows a strategy for manufacturing the hEGF synthetic gene by linking each DNA fragment of FIG. 3.

Though what has been adopted as the DNA sequence of hEGF hitherto consisted of a codon suited to an expression system such as Escherichia coli, yeast etc., the present inventors have accomplished this invention as the result of paying attention to the gene of EGF of a mouse (mEGF) which resembles closely that of a human being and completely differs from the above mentioned codon suited to the expression system in microorganisms which is quite foreign to that of a human being.

When hEGF is compared with that of a mouse [J. Scott, et al., Science, 221, 236 (1983)], it is found that they share 70 percent of homology in their amino acid sequences, with the majority of the sites where the amino acid sequences are different being caused by one point mutation of the codon.

Thus, the DNA sequence of hEGF gene is quite similar to that of a mouse. Generally, when DNA sequences of synthetic genes are derived from an amino acid sequence, it is common to adopt the codon which is most accepted in the expression system cells [Itakura et al., Science, 198, 1056 (1977)].

Current research indicates that no trouble has been experienced in expressing the eukaryote gene in prokaryote systems and in some cases a more effective result is obtained from this system than from a gene which is adapted to the expression system [M. H. Caruthers, Nucleic Acids Research, Symposium Series, 11, 197 (1982)]. While many factors are cited which improve the expression of genes, the stability of mRNA corresponding to the structural gene and the translation efficiency are very important. It is assumed in this case that high-dimensional structure determined by the mRNA sequence has a significant impact. Taking this factor into consideration, the DNA sequence of the hEGF gene should closely resemble the EGF gene of a mouse without changing its amino acid sequence. The hEGF gene of this invention was designed according to this concept and the result was that the DNA sequence of this hEGF gene showed nearly 90 percent of homology to that of the mouse. In order to construct a target gene as accurately as possible, it should be manipulated so as to minimize the existence of the comparatively long self complementary sequence on the DNA chain or the abnormal complementarity between the double strands. To satisfy these conditions a novel sequence of DNA most suitable for producing hEGF has been found as shown in FIG. 1. FIG. 1 shows the amino acid sequence in addition to the DNA sequence.

This gene can be expressed either as a fusion peptide or as hEGF as it is, without uncertain parts. In the former case, the hEGF gene may follow the DNA sequence for another protein, which begins from the 5'-terminal start codon ATG, and ends at an end codon (for example, TAG). Occasionally the hEGF gene possessing the start codon may accompany the DNA sequence for another protein with 3'-terminal end codon (for example, TAG).

For the direct expression of the latter, as shown in FIG. 2, the start codon ATG and end codon, for example TAG, are directly positioned at the 5'- and the 3'-side respectively in addition to the sequence coding for the polypeptide of hEGF, and both the 5' end and the 3' end are arranged with Eco RI and Bam HI cohesive ends respectively for insertion into a vector. A Bgl II recognition site can be established in the latter half of the structural gene to provide for gene manipulation. Likewise, a Pst I recognition site can be established downstream from the 3' end. After the sequence is modified as mentioned above, hEGF shows 80 percent of homology with EGF of a mouse (mEGF). When the hEGF gene of the present invention was synthesized, the whole hEGF gene was finally divided into 22 fragments as shown in FIG. 2, for example, and attention was paid so that a self complementary sequence would not develop at either 5'-end or the 3'-end in order to avoid self encounter of the fragments. FIG. 3 shows each such individual DNA fragment. The method of division for such fragments is not necessarily confined to the above example if attention is paid to avoiding the above mentioned self encounter possibility. The skilled artisan may suggest many other possibilities.

Each of the fragments (No. 1–No. 22) is produced according to any available synthetic method. The 5' end of each fragment is phosphorylated with polynucleotide kinase when necessary, and they are divided into 2 or 3 blocks and combined to be a double strand DNA by reaction with ligase. Furthermore, a complete hEGF gene was obtained by combining each group with DNA ligase (refer to FIG. 4).

This gene was combined with Eco RI and Bam HI digestion of pBR 322 to obtain a novel plasmid, pTB 361, with which *Escherichia coli* DH1 was transformed. The base sequence of the isolated plasmid was determined by employing a portion of fragment as primer in accordance with the Sanger method to confirm the existence of the target hEGF gene.

To express a synthetic gene of this invention it is desirable that the hEGF gene be used as a recombinant DNA inserted into a vector such as a plasmid, a bacteriophage etc.

In such a recombinant DNA it is desirable to have a promoter upstream of the start codon ATG as previously mentioned. Such a promoter may be of any kind in so far as it is appropriate for use in the host organism employed for producing transformants.

For example, for *Escherichia coli* (examples, 294, W3110, DH1, N4830, etc.), the trp promoter, lac promoter, rec A promoter, $\lambda P_L$ promoter, lpp promoter, etc. may be used; for *Bacillus subtillis* (example, MI 114, etc.), the SP 02 promoter, pen P promoter, etc. may be used; for *Saccharomyces cerevisiae* (example, AH 22, etc.) the PHO5 promoter, PGK promoter, GAP promoter, ADH promoter, etc. may be used; and for animal cell (examples, a monkey cell COS-7, a Chinese hamster cell GHO, etc.) a promoter derived from SV40 and a promoter of the LTR region derived from mouse leukemia virus (MuLV) may be used.

Particularly, the trp promoter and $\lambda P_L$ promoter are preferred when the host is *Escherichia coli*, and having an enhancer in addition to the promoter mentioned above is preferred when the host is an animal cell.

Figure 8:
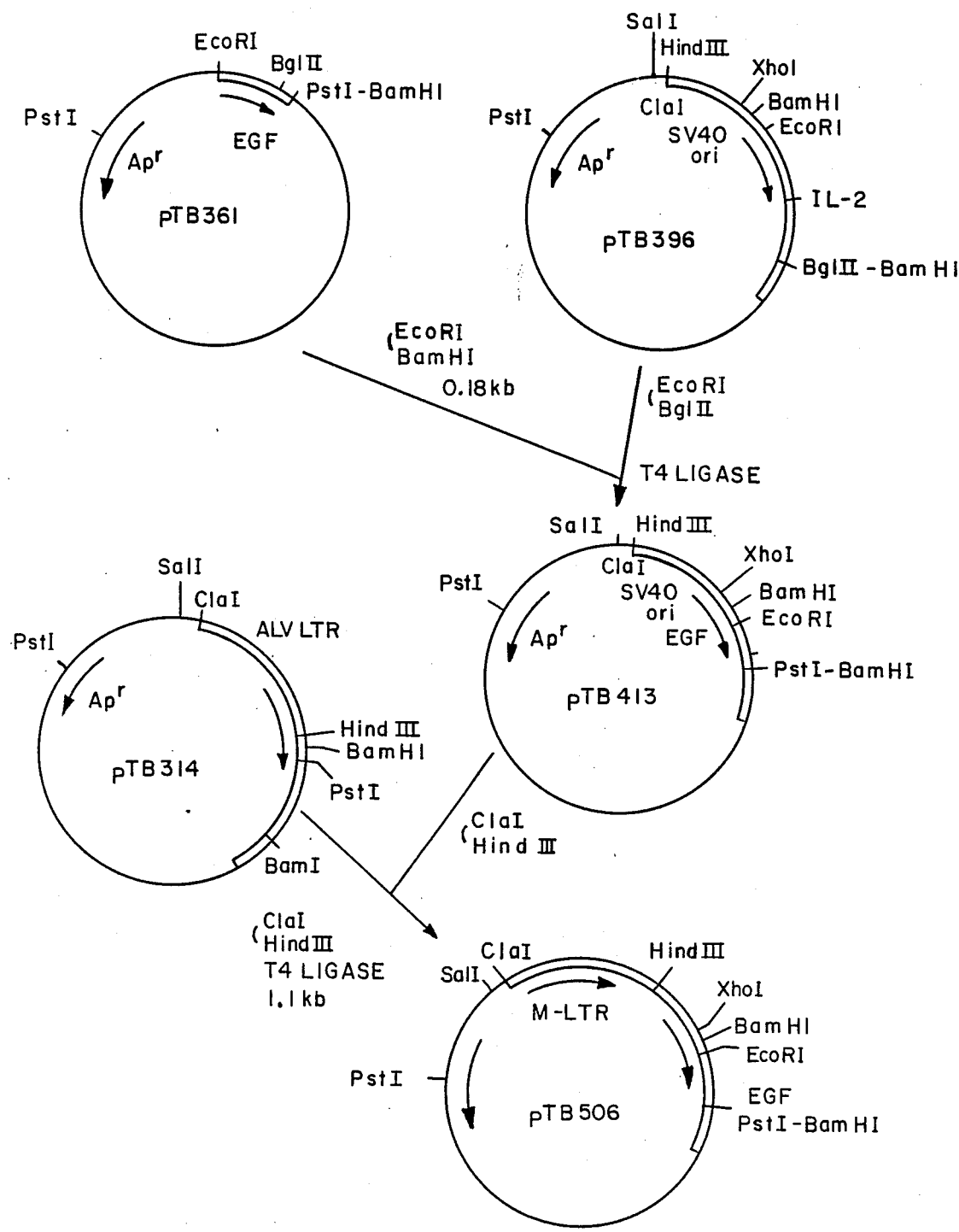
FIG. 8 shows a scheme for constructing the plasmid pTB506 for animal cell transformation as manipulated in Example 7 (i).

Examples of the expression of the hEGF synthetic gene are described below (refer to FIGS. 5, 6 and 8).

A DNA fragment with 172 base pairs cleaved from pTB 361 with Eco RI-PstI was inserted into the Eco RI, PstI site of the expression vector, ptrp 781 to obtain the expression vector pTB 370 under the control of Ptrp.

A DNA fragment with 179 base pairs obtained by digestion of pTB 361 with EcoRI-Bam HI was inserted into the EcoRI-Bam HI site of the expression vector, pTB 281 to construct an expression vector, pTB 372 under the control of $P_L$.

*Escherichia coli* DH1 was transformed with pTB 370 and the growing colony was selected by an ampicillin marker to obtain strains including the target hEGF gene.

In the case of pTB372, the temperature sensitive *Escherichia coli* N 4830 was transformed and selected by a tetracycline marker. The expression of a synthetic gene was performed by transforming *Escherichia coli* DH1 with the cloned pTB 372.

The EGF gene cleaved from pTB 361 with Eco RI-Bam HI was inserted into pTB 396, a vector for expression in an animal cell. A DNA fragment containing the LTR region (MuLV LTR) derived from mouse lukemia virus was cleaved with Cla I - Hind III and inserted upstream of the SV-40 promoter to construct pTB 506, a vector for expression in an animal cell.

A Mouse LA 9 cell was co-transformed with pTB 506 and cloned to construct a transformant, Mouse LA 9 - EGF-3 cell.

These transformants were cultured and the hEGF contained in the solution obtained by the treatment of cells with 7M guanidine was determined by the human fetal foreskin cells EGF receptor binding assay in a competitive reaction with $^{125}I$ - marked mEGF. This assay indicated a yield of more than 2 mg/1 of hEGF produced by *Escherichia coli* DH1/pTB 370 (see FIG. 1). The quantity of this expression is noteable for a direct expression of hEGF with *Escherichia coli*.

The present inventors adopted the DNA sequence of an hEGF gene bearing a strong resemblance to the DNA sequence of mEGF which resembles hEGF in terms of its amino acid sequence rather than adopting a codon best accepted by cells of the expression system. Consequently, the stability of the mRNA, the translation efficiency and the three-dimensional structure which is decided from the base sequence of mRNA, become suitable to expression, effectively producing hEGF. When the structural gene of this invention has the recognition sites, Bgl II at its latter half and Pst I near the 3' end. This method thus offers an advantage in terms of manipulation of the gene, such as the easy recognition of the performance of gene insertion, or the direction of insertion, use of a variety of vectors, etc.

Since the hEGF gene of the present invention contains a novel DNA sequence and yet it shows a strong resemblance to the DNA sequence of EGF gene of a mouse which is more akin to that of human being than are microorganisms, a high expression of hEGF was anticipated. This invention also made possible for the first time, the direct expression of hEGF using *Escherichia coli* as a host organism. Moreover, the technique of recombining DNA using the synthetic gene of this invention corresponding to hEGF offers a more efficient production of hEGF compared with previous methods and thus contributes to the production of hEGF for use as a pharmaceutical agent. The elucidation of the role of hEGF within living cells, of hEGF ascertaining the mechanism of in developing and controlling cells and, determining the mechanism of the development of cancer, may all be assisted by the availability of large quantities of hEGF.

EXAMPLES

What follows is the description of the present invention by way of examples which are intended to aid in the understanding of the present invention, but which are not to be construed as limitations thereof. All percentages reported herein are percent by weight, unless otherwise specified. All temperatures are expressed in degrees Celsius.

Recombinants shown below, i.e., *Escherichia coli* DH1/pTB 370 and *Escherichia coli* DH1/pTB 372, pRK 248 cIts have been deposited with the Institute for Fermentation (IFO) under Accession Nos. IFO-14379 and IFO-14380 and also with Fermentation Research Institute, Agency of Industrial Science and Technology, Ministry of International Trade and Industry, Japan (FRI) under the respective Accession Nos. FERM P-7883 and FERM P-7884 since Oct. 5, 1984, which having been converted to deposits under the Budapest Treaty, are stored at the FRI under the respective Accession Nos. of FERM BP-843 and FERM BP-844, and Mouse LA9-EGF-3 has been deposited with the IFO under No. IFO-50055.

EXAMPLE 1

Synthesizing DNA Fragments

Each DNA fragment was synthesized in accordance with solid phase synthesis of phosphotriestel method [Ito, H. et al., *Nucl. Acids Res.*, 10, 1755 (1982)]. Dimer blocks used for synthesis were synthesized according to the method of Broka et al *Nucl. Acids Res.*, 8, 5461 (1980)] or purchased commercially (Wako Pure Chemical, Japan), which was powdered in the mixed solution of pentane and diethyl ether (1:1, v/v) after dissolving it into the mixed solution of pyridine (Py), triethylamine (TEA), water (3:1:1, v/v) and removing cyanoethyl radical.

The following is the synthetic process for DNA fragments:

25 mg of 1 percent polystyrenes (Bachem Fine Chemical) with dimethoxytritylnucleoside was treated with reagent in the following order.

(1) With 3 percent (w/v) trichloroacetic acid (TCA) in dichloromethane [Tanaka, T. et al., *Nucl. Acids Res.*, 10, 3249 (1982)] for one minute X2 (X2 indicates same manipulation was repeated twice).
(2) Dichloromethane: X4
(3) Pyridine: X3
(4) 0.3 ml of dry pyridine containing 20 mg of dinucleotide block or 30 mg of monomer block
(5) Concentration of the above solution under reduced pressure.
(6) At 40° C. for 20 minutes with 0.3 ml of dry pyridine containing 25 mg of mesitylene-sulfonyl-nitro-triazolide and 5 mg of nitro-triazole
(7) Pyridine X2
(8) With 2 ml of pyridine containing 10 percent (v/v) acetic anhydride and 0.1M of dimethylamino-pyridine (DMAP) for 2 minutes
(9) Pyridine X2
(10) Dichloromethane X3.

Through repetition of this process for a cycle of 40 minutes with the proper nucleotide or mononucleotide block, a target oligonucleotide chain was constructed. After the synthesis, the resin was treated with 0.5M of 1, 1, 3, 3-tetramethyl-guanidinium-pyridine-2-aldoxime [Reese, C. B., et al., *Tetrahedron Lett.*, 2727 (1978)] at 40° C. for 14 hours to extract the target object from its polymer carrier and treated with concentrated aqueous ammonia at 60° C. for 4 hours to remove all protecting groups except dimethoxytrityl. This sample was applied to a reversed phase $C_8$ silica gel (Ricroprep RP-8, Merck) column [3.0(diameter)×2.0(length) cm] and the effluent eluted with 30 percent acetonitrile was treated with 80 percent acetic acid at room temperature for 15 minutes. This sample, after wash with ether, was purified [Gait M. J. et al., J. C. S., Chem. Commun., 37 (1982)] via ion exchange high performance liquid chromatography [Partisil 10 SAX, Whatman] to obtain pure DNA fragments. The 22 types of DNA fragments thus obtained are shown by FIG. 3.

EXAMPLE 2

Phosphorylating Oligo DNA

Each DNA fragment was reacted in 25 $\mu$l of phosphorylating solution [2.5 $\mu$g of oligo DNA, 50 mM Tris-HCl, pH 7.6, 10 mM $MgCl_2$, 10 mM 2-mercaptoethanol, 1 mM ATP, 2.5 unit of T4 polynucleotide-kinase (Takara Shuzo, Japan)] at 37° C. for 1 hour. The reaction mixture was frozen before using.

EXAMPLE 3

Connecting DNA Fragments

A series of the steps for constructing a double strand of hEGF gene are shown by FIG. 4 (←mark in the figure indicates that the 5' end hydroxyl is phosphorylated). For example, the connection of block I was performed as follows. Each 5 $\mu$l of phosphorylated solution of 12 types of DNA fragments (corresponding to each of DNA 1 through 12) obtained in Example 2 was added one after another, to be 60 $\mu$l, and 1.4 units of T4 DNA ligase (Takara Shuzo, Japan) was added to this solution. After incubation at 14° C. for 25 hours the ligation solution was treated at 65° C. for 10 minutes to stop the reaction.

Then to the digested dimers of block I which became main products with restriction endonuclease Eco RI (Takara Shuzo, Japan), the following three ingredients, 50 mM NaCl, 0.01% Bovin serum albumin (BSA) and 7 mM $MgCl_2$ were added. This reaction solution was kept under the reaction of 120 units of Eco RI at 37° C. for 1.5 hours and electrophoresed in buffer solution (pH 8.3) [100 mM Tris-HCl, 100 mM boric acid, 2 mM EDTA] using 6 percent concentration acrylamide gel at 25 mA for 1.5 hours. After the electrophoresis, the gel was stained with 0.6 mg/l of ethidium bromide (EtBr) and a gel slice containing 101 bp of DNA fragments was closed up in a dialysis tube containing an electrophoresis buffer solution to elute the DNA fragments electrically (J. Mol. Biol., 110, 119 (1977)]. After this solution remained in the dialysis tube it was extracted three times with phenol saturated with 0.01M Tris-HCl, (pH 7.6), 0.1M NaCl and 0.001M EDTA and further with diethyl ether, NaCl was added up to 0.2M which was followed by addition of cold ethanol twice as much in quantity to precipitate the DNA at $-20°$ C. Block II (containing No. 13 through 22) was prepared by a process similar to the above.

EXAMPLE 4

Figure 5:
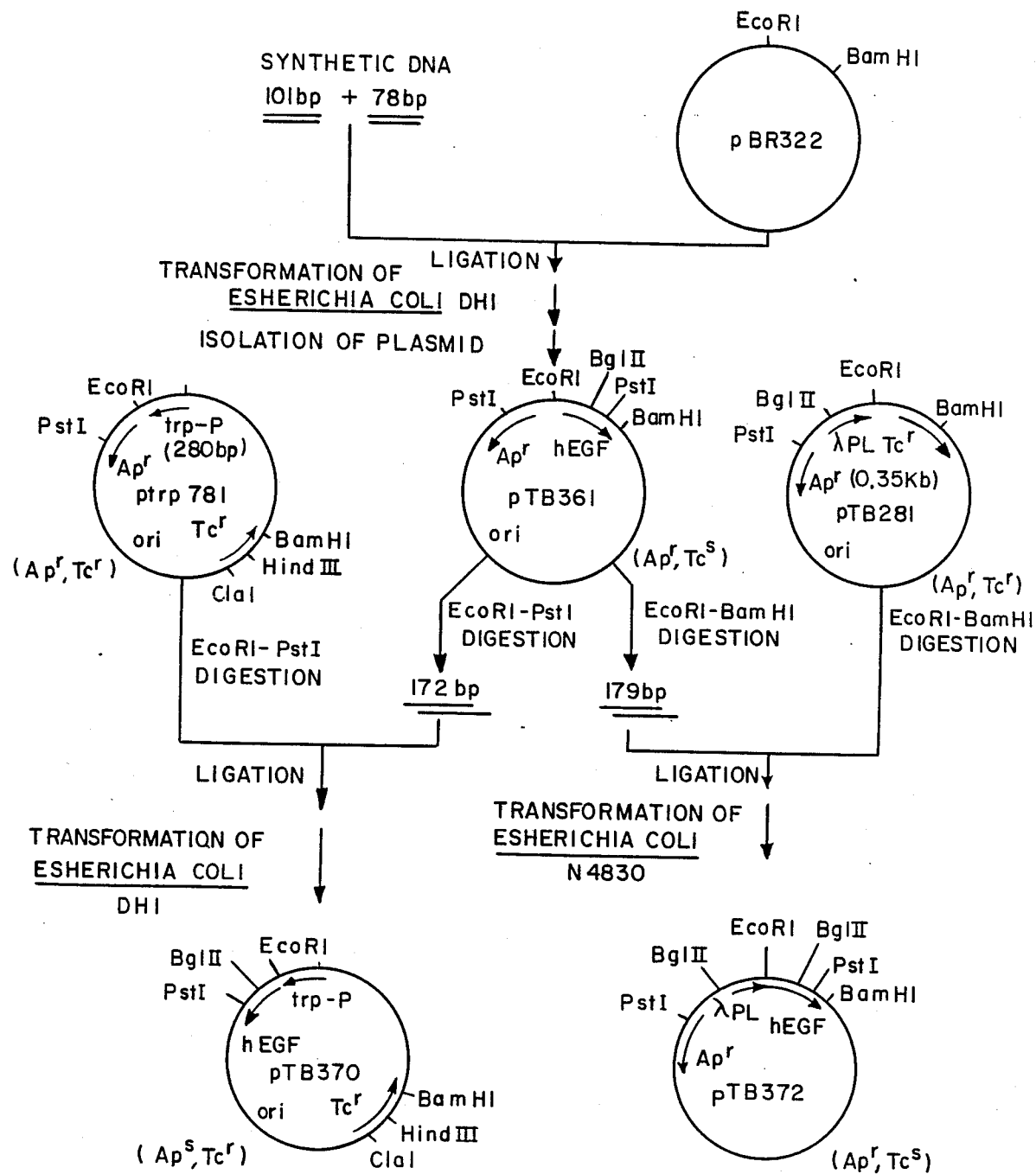
FIG. 5 is a scheme for producing an expression plasmid having the synthetic hEGF gene of the present invention.

Cloning of hEGF genes (FIG. 5)

Plasmid pBR 322 of *Escherichia coli* was used as the cloning vector. After pBR 322 DNA was kept under reaction of 20 μl of reaction solution [10 mM Tris-HCl, pH 8.0, 7 mM $MgCl_2$, 100 mM NaCl, 2 mM 2-mercaptoethanol, 0.01% bovin serum albumin (BSA), 19 units of Eco RI (Takara Shuzo, Japan), 5 units of Bam HI (Takara Shuzo, Japan)] at 37° C. for 1 hour, it was diluted with three times as much water and treated at 65° C. for 10 minutes to inactivate the enzyme. 0.5 μl of the digestion solution was mixed with approx. 20 equivalent of DNA fragment block I and II, and by using this as 10 μl reaction solution in the presence of 66 mM Tris-HCl (pH 7.5), 6.6 mM $MgCl_2$, 10 mM dithiothreitol (DDT) and 1 mM ATP, the hEGF gene was combined with plasmid by reaction with T4 DNA ligase (New England Bio Labs) at 14° C. for 2 hours.

*Escherichia coli* DH1 strain [Selson, M. E. et al., *Nature*, 217, 1110–1114 (1968)] was transformed with the solution mentioned above by a known method. That is, after 50 μl of competent cell [Hanahan, D., *J. Mol. Biol.*, 166, 557 (1983)] preserved at $-70°$ C. was incubated at 0° C. for 15 minutes, 4 μl of the above reaction solution was added. After the competent cell was again incubated at 0° C. for 30 minutes, it was kept at 42° C. for 1.5 minutes and then for another 5 minutes at 0° C. 200 μl of LB medium (10 g of vacto trypton, 5 g of extract from vacto yeast, 8 g of NaCl are included per liter) was added to this reaction solution and incubated at 37° C. for 50 minutes. These *Escherichia colis* were scattered over an LB agar plate containing 35 μg/ml of ampicillin and cultured at 37° C. for one night. 60 strains were selected from the cultured ampicillin resistant colonies and were seeded in an LB agar plate containing 7 μg/ml of tetracycline but 59 strains did not develop. Then 16 strains out of the 59 were selected and the plasmid DNA's of the transformants were roughly purified by the alkali method [Maniatis, T. et al., *Molecular Cloning* (Cold Spring Harbour), 368–369 (1982)], and digested with Eco RI and Bam HI, Eco RI and Bgl II, and Pst I. It became clear by 2% agarose gel electrophoresis of the digests 14 strains were transformed with hEGF genes inserted appropriately in the vector. The cloning vector thus obtained has been named pTB 361.

One platinum spoonful of *Escherichia coli* DH1 containing plasmid pTB 361 was seeded in 1.5 ml of LB medium containing 35 μg/ml of ampicillin and shake cultured at 37° C. for one night. 0.3 ml of this culture solution was added to 25 ml of the same medium in a 200 ml flask and shake cultured at 37° C. for 6.5 hours. This culture solution was added to 125 ml of the same medium of 125 ml which had been separately poured in a 500 ml flask and shake cultured for another 45 minutes. Then chloramphenicol was added up to 170 μg/ml and cultured for one night to amplify plasmid DNA. 150 ml of this culture solution was centrifuged at 6,000 rpm at 4° C. for 9 minutes. Bacteria thus obtained were washed with isotonic sodium chloride solution and suspended with 4 ml of lysozyme solution [25 mM Tris-HCl, pH 8.0, 50 mM glucose, 10 mM EDTA, 1 mg/ml lysozyme]. After ice cooling for 20 minutes, 8 ml of alkaline solution [1% (w/v) SDS, 0.2N NaOH] was added and the mixture was kept in ice for another 5 minutes. After 6 ml of 5M potassium acetate buffer solution (pH 4.8) was added, the neutralizate was kept in ice for 10 minutes and centrifuged at 10,000 rpm and 4° C. for 20 minutes. The supernatent diluted with ethanol (twice as much in quantity) was shaken, and kept at $-20°$ C. for 10 minutes to be centrifuged at 10,000 rpm and 4° C. for 20 minutes. The precipitate, after being dried in the air, was dissolved with 4 ml of buffer solution [1 mM $Na_2EDTA$ (pH 8.0), 10 mM Tris-HCl (pH 8.0)] and 3.9 g of cesium chloride (CsCl) and 3 mg of EtBr were added. Then it was applied to CsCl-EtBr equilibrium density gradient centrifugation using Beckman 50 Ti Rotor at 35,000 rpm and 15° C. for 64 hours. Plasmid DNA bands were collected, twice as much buffer solution [1 mM $Na_2EDTA$, pH 8.0, 10 mM Tris-HCl, pH 8.0] was added and then washed twice with the same quantity of chloroform phenol (1:1, v/v) to remove EtBr. The DNAs were precipitated with ethanol. The precipitated DNA were dissolved in 0.6 ml buffer solution [1 mM EDTA, 10 mM Tris-HCl, pH 8.0, 0.3 M NaCl] and was reprecipitated with ethanol.

Here the base sequence of hEGF gene which was inserted into isolated plasmid pTB 361 was confirmed using the method of Wallace et al [*Gene*, 16, 21–26 (1981)]. Namely, pTB 361 DNA was kept under the reaction of 10 μl of reaction solution [7 mM Tris-HCl, pH 7.5, 7 mM $MgCl_2$, 50 mM NaCl, 4 unit Pvu II (Takara Shuzo, Japan)] at 37° C. for 1 hour. After 1 μl of aqueous solution (1.0 $A_{260}$/ml) of DNA fragment No. 7 was added to this reaction solution as primer and heated at 100° C. for 5 minutes, it was promptly cooled in ice. The following reaction was worked as ordinary dideoxy method. The accuracy of the base sequence of hEGF gene was also confirmed by using DNA fragment No. 14 and 18 as primers.

EXAMPLE 5

Construction of Expression Plasmid for hEGF and Production of Transformant (FIG. 5)

(i) After 10 μg of pTB 361 obtained by the above Example 4 was kept under a reaction solution [50 mM NaCl, 6 mM Tris-HCl (pH 7.6), 6 mM $MgCl_2$, 6 mM 2-mercaptoethanol, 0.01% BSA, 50 units Eco RI, 10 units Pst I (Takara Shuzo, Japan) ] at 37° C. for 1.5 hours, 172 bp DNA fragments were purified according to a normal method (supra) by 2% agarose gel electrophoresis. On the other hand, ptrp 781 [Kurokawa, T. et al., *Nucl. Acids Res.*, 11, 3077–3085, (1983)] was used as expression vector. ptrp 781 DNA was digested with Eco RI and Pst I in the same manner mentioned above and twice as much water was added to this reaction solution and the solution was kept at 65° C. for 10 minutes to inactivate enzyme.

The 172 bp DNA and plasmid DNA thus obtained respectively have a cohesive end of a single strand created by the digestion with Eco RI and Pst at both ends.

Both were mixed and combined with T4DNA ligase (NEB) at 14° C. for 5.5 hours in the presence of 66 mM Tris-HCl, pH 7.5, 6.6 mM MgCl$_2$, 10 mM DTT and 1 mM ATP to transform *Escherichia coli* DHI strains in the same method previously mentioned. Then these *Escherichia colis* were scattered over an LB agar plate containing 7 μg/ml of tetracycline and cultured at 37° C. for one day. Tetracycline resistant colonies thus obtained were seeded in an LB agar plate containing 35 μg/ml of ampicillin to select transformed strains which did not grow. And, in the same manner as mentioned above the plasmid DNAs of the transformant were digested with Eco RI and Pst I, and further with Bgl II and Hind III to choose transformed strains with hEGF gene properly inserted into. The expression plasmid thus obtained has been named pTB 370 and its transformant *Escherichia coli* DH1/pTB 370.

Figure 6A:
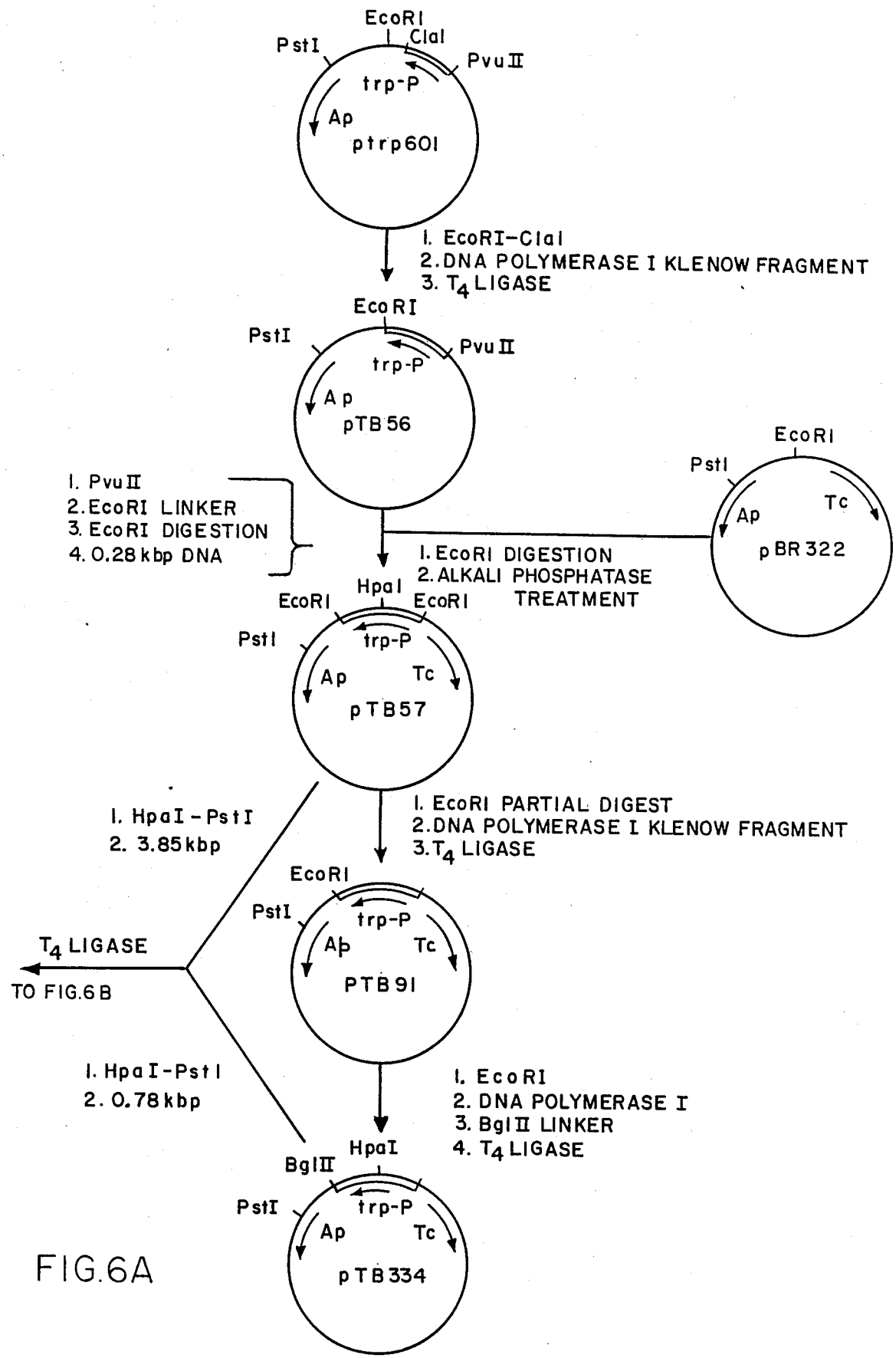
FIG. 6 is a scheme for producing an expression vector containing a promoter.
Figure 6B:
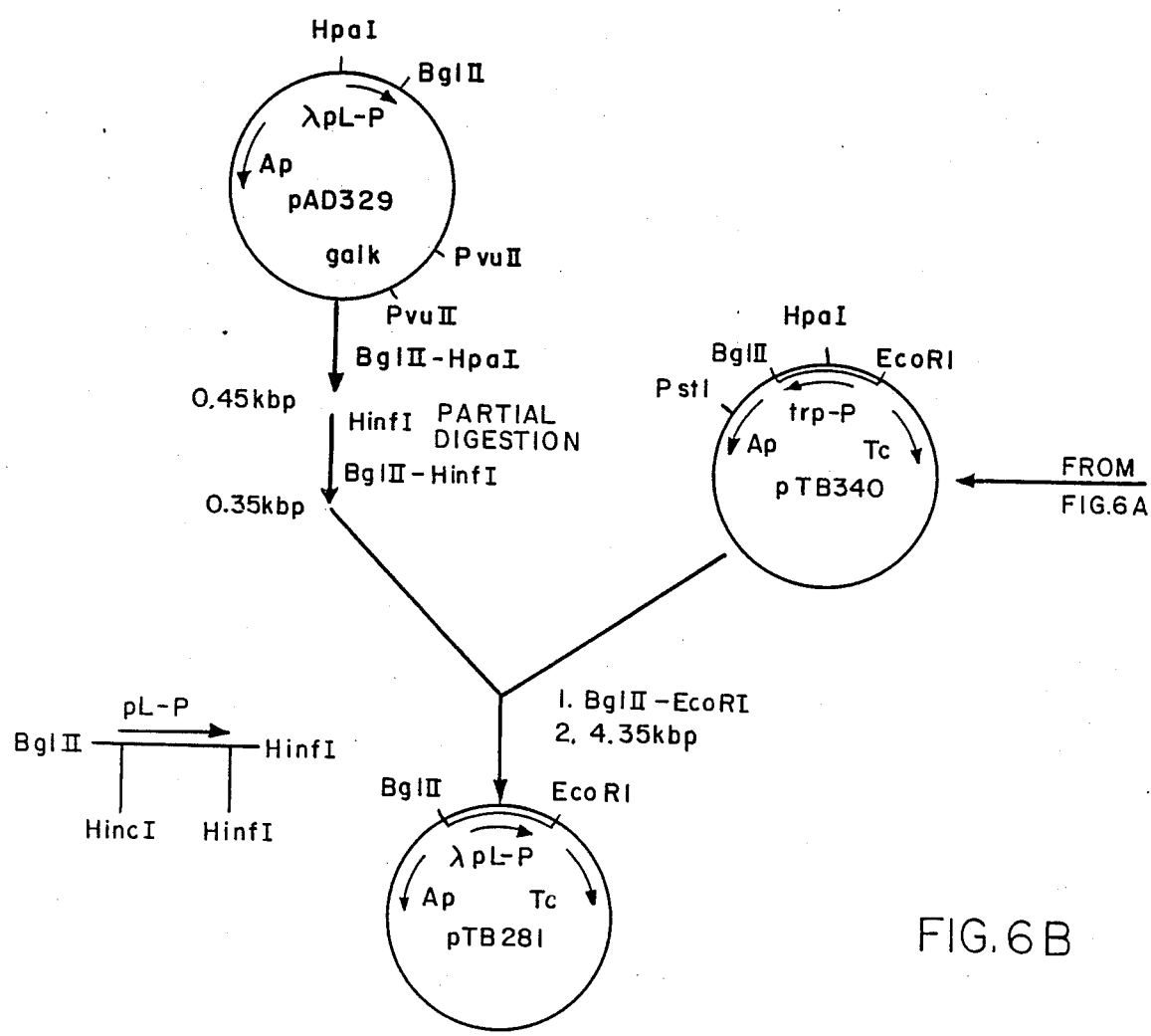

(ii) An expression vector containing the λP$_L$ promoter was constructed as follows (FIG. 6).

After plasmid ptrp 601 [Y. Fujisawa et al., Nucleic Acids Res., 11, 3581 (1983)] was cleaved with restriction enzymes, Eco RI and Cla I, the cohesive ends of a single strand produced were filled with DNA polymerase I (Klenow fragment), treated with phenol and precipitated with ethanol. This straight chain DNA was altered to a circular DNA at 14° C. by reaction with T4 DNA and *Escherichia coli* was transformed by the same method mentioned previously. A plasmid with Eco RI site at downstream of trp promoter was isolated and has been named pTB 56.

After this plasmid pTB 56 was digested with Pvu II to make it a straight chain DNA, it was mixed with synthetic oligonucleotide (Eco RI linker) and kept under the reaction with T4 DNA ligase. After the reaction product was digested with Eco RI, about 0.28 kbp DNA fragments containing trp promoter gene were purified by 2% agarose gel electrophoresis according to a known method.

On the other hand, after pBR 322 DNA was digested with Eco RI to make it a straight chain DNA, the phosphate residue at 5' end was removed by the treatment with alkaline phosphatase and the hydrolysate was mixed with the 0.28 kbp DNA Eco RI fragments above mentioned, and T4 DNA ligase at 14° C. to give a circular DNA, with which *Escherichia coli* was transformed. A plasmid with trp promoter cloned at the Eco RI site of pBR 322 was isolated from the transformed *Escherichia coli* and has been named pTB 57.

After the straight chain DNA obtained by a partial digestion of this plasmid pTB 57 with EcoRI was manipulated in the same manner previously mentioned and one of the EcoRI recognition sites was destroyed to make the DNA circular, *Escherichia coli* was transformed with the circular DNA. A plasmid was obtained from the colony thus prepared and the plasmid which was recognized by the pattern of the digestion by restriction enzyme by the lack of an EcoRI recognition site, located upstream of trp promoter, has been named pTB91.

After the plasmid pTB 91 was digested with EcoRI, the cohesive end of a single strand was filled in with DNA polymerase I and mixed with synthetic oligonucleotide (Bgl II linker) and then combined by the use of T4 DNA ligase. This plasmid in which BglII site was introduced downstream of the trp promoter has been named pTB 334.

By using pTB57 and pTB334 thus obtained a plasmid with an EcoRI recognition site upstream of the trp promoter and Bgl II recognition site downstream was constructed. First of all, after pTB344 was cleaved with restriction enzymes, Hpa I and Pst I, about 0.78 kbp of DNA fragments were eluted and purified by 2% agarose gel electrophoresis.

On the other hand, pTB57 was cleaved with the same restriction enzymes and then 3.85 kbp of DNA fragments were eluted and purified by 1% agarose gel electrophoresis. Afterwards, both were mixed and combined by reaction with T4 DNA ligase. *Escherichia coli* were transformed with the obtained DNA. Plasmids were obtained from the colony thus obtained and transformed strains containing a target plasmid were selected using the pattern of cleavage with restriction enzyme. A plasmid isolated from the strain has been named pTB 340. 0.35 kbp of DNA fragments containing the λP$_L$ promoter were isolated from plasmids pAD329 [Adhya, S. et al., Cell, 29, 939–944 (1982)] containing the λP$_L$ promoter. To begin with, plasmid pAD329 was digested with restriction enzymes, Bgl II and Hpa I and then, applied to 2% agarose gel electrophoresis to elute and purify about 0.45 kbp of DNA fragment. After this 0.45 kbp of DNA fragment was partially digested with Hinf I, they were electrophoresed with 2% agarose gel to elute and purify about 0.35 kbp which contains an cohesive ends at their both ends caused by digestion with Bgl II and Hinf I.

On the other hand, plasmid pTB340 were digested with restriction enzymes, Bgl II and Eco RI and then about 4.35 kbp of DNA were eluted and purified by 1% agarose gel electrophoresis. DNA thus obtained contained cohesive ends at their both ends caused by digestion with Bgl II and Eco RI. After 0.35 kbp of DNA fragment containing the λP$_L$ promoter thus obtained were mixed with about 4.35 kbp of DNA and changed to circular DNA with T4 DNA ligase, *Escherichia coli* was transformed with the DNA. A plasmid containing the λP$_L$ promoter with Bgl II recognition site upstream and Eco RI recognition site downstream was isolated from the *Escherichia coli* transformant and has been named pTB281.

An expression plasmid for hEGF was constructed using this pTB281 (FIG. 5). First, 10 μg of plasmid pTB361 described in Example 4 was allowed to react with restriction enzymes in reaction solution [100 mM NaCl, 10 mM Tris-HCl, pH 8.0, 7 mM MgCl$_2$, 2 mM 2-mercaptoethanol, 0.01% BSA, 50 units Eco RI, 20 units Bam HI (Takara Shuzo, Japan)] at 37° C. for 1.5 hours and then, 179 bp of DNA fragments containing the hEGF gene were eluted and purified by 2% agarose gel electrophoresis. Plasmid pTB281 was also digested with Eco RI and Bam HI in the same manner described above and kept at 65° C. for 10 minutes with twice as much water added to inactivate enzyme. Those both were mixed and combined using T4 DNA ligase at 14° C.

Transformation of *Escherichia coli* was performed as follows. LB medium was added to the overnight culture of *Escherichia coli* N4830 strain (Pharmacia, Japan) and diluted 100 times. After the dilution was shake cultured at 37° C. for 2 hours, it was centrifuged at 3,300 rpm and 4° C. for 8 minutes and strains thus obtained were washed with 10 mM NaCl 50 mM CaCl$_2$ solution was added to the strains and kept in ice for 15 minutes to be centrifuged at 3,300 rpm and 4° C. for 4 minutes and to be suspended again with 100 μl of 50 mM CaCl$_2$. This suspension of *Escherichia coli* N4830 to which 7 μl of the ligation solution above obtained was added, was incubated at 0° C. for 45 minutes, and then at 37° C. for 2 minutes. After 900 μl of LB medium was added, it was incubated at 30° C. for 1 hour. These *Escherichia coli* were spread over LB agar plate containing 35 μg/ml of ampicillin and cultured at 30° C. for one night. All of the ampicillin resistant colonies lost their resistance ability against 7 μg/ml of tetracycline. Then plasmid DNA was extracted from a part of this transformed strain and digested with Eco RI and Bam HI and also with Bgl II to select a transformed strain with the hEGF gene inserted properly. A plasmid thus obtained has been named pTB372.

pTB372 obtained as mentioned above was used for transforming *Escherichia coli* DH1 strain containing pRK248cIts (repressor) [Bernard, H. et al., *Methods in Enzymology*, 68, 482–492 (1979)] in the same manipulation previously mentioned. Transformants thus obtained were spread over an LB agar plate containing 35 μg/ml of ampicillin and 7 μg/ml of tetracycline and cultured at 30° C. for one night. Plasmid DNA obtained from developed colonies in the same manner previously mentioned was digested with restriction enzyme to select a transformed strain containing hEGF using the digestion pattern. The transformed strain has been named *Escherichia coli* DH1/pTB372. pRK248cIts.

EXAMPLE 6

Production Method of hEGF (i) *Escherichia coli* DH1/pTB 370 was shake cultured in LB medium containing 7 μg/ml of tetracycline at 37° C. for 1 night. After 10 ml of M9 medium [0.4% Casamino acid, 1% glucose] containing 7 μg/ml of tetracycline was added to 0.5 ml of the above culture solution and was shake cultured at 37° C. for 4 hours, 3-β-indoleacrylic acid (IAA) was added to be 30 μg/ml. After the cultivation had been continued for 4 more hours, 10.5 ml of this culture solution was centrifuged at 7,000 rpm and 4° C. for 10 minutes and the strains thus obtained were frozen at −70° C. This was dissolved and incubated in 1 ml of reaction solution [7M guanidin hydrochloride, 2 mM phenylmethylsulfonyl fluoride (PMSF), 0.1M Tris-HCl, pH 7.0] at 0° C. for 1 hour. This reaction solution was centrifuged at 20,000 rpm and 4° C. for 30 minutes. The supernatant thus obtained was dialyzed twice against 1 liter of TEN [20 mM Tris-HCl, pH 8.0, 1 mM EDTA. 0.2M NaCl] at 4° C. and the precipitated insoluble substance was removed by centrifugation at 20,000 rpm and 4 ° C. for 30 minutes. The solution thus obtained was stored at −20° C.

(ii) *Escherichia coli* DH1/pTB 372, pRK248cIts was cultured under shaking in M9 medium containing 35 μg/ml of ampicillin and 7 μg/ml of tetracycline at 29° C. for one night. 10 ml of M9 medium containing 35 μg/ml of ampicillin was added to 0.5 ml of this culture solution to culture under shaking at 29° C. for 4 hours. After this shake culture was followed for another 2 hours at 42° C., it was treated same as previously mentioned and the solution thus obtained was stored at −20° C.

Each product obtained by (i) and (ii) above was analyzed by Radio Receptor Assay Method (RRA Method) [Cohen, S. et al., *Proc. Natl. Acad. Sci. USA*, 72, 1317–1321 (1975)].

EGF activity was indicated by the standard weight of purified mouse EGF showing an identical activity. The epidermal cell of human embryo, Flow 7000 (Flow Laboratories, Inc.) was cultured in a cell culture dish of 1.6 cm in diameter (Linbro, Flow Laboratories, Inc.) using Dulbecco Minimal Essential Medium (DMEM) containing 10% bovin embryo serum. This medium was discarded. After the cells were washed in the DMEM medium containing 0.1% BSA, 0.2 ml of the above medium, 5 ng of mouse EGF (Collaborative Research, Inc.) labelled with $^{125}$I by the chloramine T Method and a reasonable amount of each product obtained in the above manner were added to the cells and they were cultured at 37° C. for 1 hour. The cells after being washed in the medium, were treated with 0.2N NaOH and transferred to a tube to measure the degree of $^{125}$I taken in with γ ray counter. The quantity of human EGF contained in the product was calculated from the weight inspection curve obtained in the similar manner by the competitive reaction with the mouse EGF whose weight was already known. The following Table 1 shows the result.

TABLE 1

| Expression of Human EGF Gene in *Escherichia Coli* | |
|---|---|
| Samples | Determination by RRA Method |
| i Extractive of *E.Coli* DH1/pTB 370 Strain | 2.2 (μg/ml) |
| ii Extractive of *E.Coli* DH1/pTB 372, pRK 248 cIts | 0.44 (μg/ml) |

Figure 7:
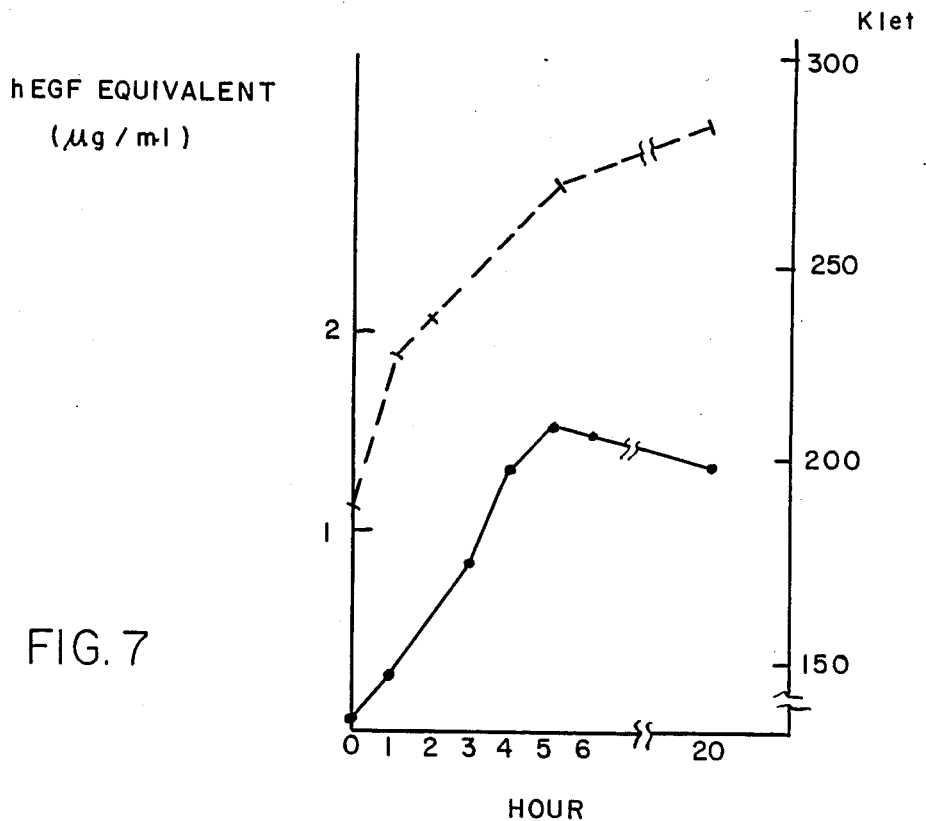
FIG. 7 is a graph which indicates the growth of transformants and the EGF activity as an example of the methods of the present invention.

After the culture of *Escherichia coli* DH1/pTB 370 strains and induction by IAA, the EGF activity in the cell extracts as well as its growth was measured in the method already described. The result is shown by FIG. 7. In the drawing the dotted line shows the growth of strains and the regular line the EGF activity.

EXAMPLE 7

Production of hEGF in Animal Cells (i) Construction of Plasmid pTB 506

By using pTB 106 [United States Patent Application Ser. No. 745,796 Specification Example (i)] containing SV 40 promoter and IL-2 gene, the Pst I cleavage site located at the 5' end of the IL-2 gene region was altered to the Eco RI cleavage site and constructed was plasmid pTB 396 with Bgl II cleavage site inserted at the immediate front of the Bam HI cleavage site located at the 3' end of the above gene region.

This pTB 396 was cleaved with Eco RI and Bgl II to give the plasmid DNA deleted IL-2 gene region from the pTB 396. On the other hand, pTB 361 was cleaved with Eco RI and Bam HI to take out EGF gene. This gene was combined with the above plasmid DNA using T4DNA ligase to construct pTB 413. Then, DNA fragments containing LTR region of Evelson mouse leukemia virus (MuLV) [Goff, S. P. et al, *Cell*, 22: 777–785 (1980)] were isolated from pTB 314 [United States Patent Application Ser. No. 745,796 Specification Example 1 (iii) ] by cleavage with Cla I and Hind III and inserted into the cleaved sites of pTB 413 cleaved with Cla I and Hind III to construct pTB 506 (FIG. 8).

(ii) Transformation of Animal Cells

Dulbecco changed Eagle MEM medium containing 10% Bovine embryo serum was put into Falcon schale (6 cm in diameter) and mouse HPRT (hypoxanthine phosphoribosyl transferase) defected L cells (LA 9 cells) [Littlefield, J. W., *Experiment Cell Research*, 41: 190–196 (1966)] were cultured at 7° C. overnight. After the culturing, to these cells ($7 \times 10^5$/dish), 0.5 μg of plasmid p4aA8 (plasmid containing human HPRT cDNA) [Jolly, D. J. et al., *Proceeding of National Academy of Science USA*, 80: 477–481 (1983)] and 10 μg of pTB 506 DNA were mixed and inoculated in accordance with the method by Graham et al. [Virology, 52: 456–467 (1973)] for cotransformation. After culturing at 37° C. for 4 hours the medium was renewed to be cultured for one night. On the following day the medium was again renewed with HAT medium (Dulbecco changed Eagle MEM medium containing 15 μg/ml hypoxanthine, 1 μg/ml aminopterin, 5 μg/ml thymidine) containing 10% of bovin embryo serum for continued culture at 37° C.

When the culture was kept on by renewing culture solution once in every few days, cells obtaining the charactor of HRRT+ increased and formed colonies in 2 to 3 weeks.

(iii) Cloning of Transformants and Quantitative Analysis of EGF

Transformed cells obtained by Example 7 (ii) were cloned according to the limited dilution method. After cloning, the cloned cells were cultured in Eagle changed MEM medium containing 10% Bovin embryo serum. Separated cloned cells were spread in a Falcon dish (6 cm in diameter). When cells became confluent, they were peeled off with a rubber policeman and gathered by centrifugation (2000 rpm×5 minutes). Then, 200 μl of NET was added to the cells thus gathered and the cells were ruptured by supersonic treatment (5 second×2). After the broken cells were centrifuged (20,000 rpm at 4° C. for 30 minutes), the activity of EGF in the supernatant was measured by the method of Sample 6. It became clear that mouse LA9-EGF-3 cells of transformed cell clones produced 1.4 ng/$10^7$ cells of EGF. The result is shown by Table 2.

TABLE 2

| | Expression of Human EGF Gene in Mouse Cell | |
|---|---|---|
| | Samples | Quantitative Analysis by RRA Method |
| i | Extractive of Mouse LA9-EGF-3 | 1.4 (ng/$10^7$ cells) |
| ii | Extractive of Mouse LA9 | <0.1 (ng/$10^7$ 7 cells) |

The following references, which are referred to for their disclosures at various points in this application, are incorporated herein by reference.

Ann. Rev. Physiol., 43, 251 (1981)
Nature, 257, 325 ('75)
Nucleic Acids Research 10, 4467 ('82)
EP Patent Provisional Publication No. 89 626
Proc. Natl. Acad. Sci. U.S.A. 80, 7461 ('83)
Science, 221, 236 ('83)
Science, 198, 1056 (1977)
Nucleic Acids Research, Symposium Series, 11, 197 ('82)
Nucl. Acids Res., 10, 1755 (1982)
Nucl. Acids Res., 8, 5461 (1980)
Tetrahedron Lett., 2727 (1978)
J. C. S., Chem. Commun., 37 (1982)
J. Mol. Biol., 110, 119 (1977)
Nature, 217, 1110–1114 (1968)
J. Mol. Biol., 166, 557 (1983)
Molecular Cloning (Cold Spring Harbour), 368–369 (1982)
Nucleic Acids Res., 11, 3581 (1983)
Cell, 29, 939–944 (1982)
Methods in Enzymology, 68, 482–492 (1979)
Proc. Natl. Acad. Sci. USA, 72, 1317–1321 (1975)
Cell 22: 777–785 (1980)
Experiment Cell Research 41: 190–196 (1966)
Proc. Natl. Acad. Sci. USA, 80: 477–481 (1983)
Virology 52: 456–467 (1973).

What is claimed is:

1. A synthetic DNA sequence which encodes the polypeptide, human epidermal cell growth factor, said DNA sequence being represented by:

AACAGTGATTCAGAATGTCCTCTCTCACACGATGGAT
ACTGCCTCCATGACGGCGTGTGTATGTATATTGAAGC
ACTAGACAAATACGCATGCAACTGTGTAGTTGGCTAT
ATTGGTGAACGATGCCAGTACCGAGATCTGAAATGGT
GGGAACTGCGA.

2. A recombinant expression vector comprising the DNA sequence according to claim 1, inserted under the operative control of a promoter in said expression vector.

3. The synthetic DNA sequence according to claim 1, which further comprises the start codon ATG at its 5'-terminal end.

4. The DNA sequence according to claim 3, which further comprises a DNA promoter sequence operatively located upstream of the start codon ATG.

5. The DNA sequence according to claim 4, wherein the promoter is a promoter recognized by the host cell, *Escherichia coli*.

6. The DNA sequence according to claim 5, wherein the promoter recognized by the host cell *Escherichia coli*, is the trp promoter.

7. The DNA sequence according to claim 5, wherein the promoter recognized by the host cell *Escherichia coli*, is the $P^1$ promoter.

8. The DNA sequence according to claim 4, wherein the promoter is a promoter recognized by host cells which are animal cells.

9. The DNA sequence according to claim 8, wherein the promoter recognized by animal cells is derived from SV40.

10. The DNA sequence according to claim 9, which further contains a promoter of the LTR region derived from mouse leukemia virus.

11. The DNA sequence according to claim 8, which further contains an enhancer operably linked to the promoter.

12. A method for producing a synthetic DNA sequence which encodes the polypeptide, human epidermal cell growth factor, said DNA sequence being represented by:

AACAGTGATTCAGAATGTCCTCTCTCACACGATGGAT
ACTGCCTCCATGACGGCGTGTGTATGTATATTGAACG
CACTAGACAAATACGCATGCAACTGTGTAGTTGGCTA
TATTGGTGAACGATGCCAGTACCGAGATCTGAAATGG
TGGGAACTGCGA, which method comprises enzymatically combining two or more oligodeoxynucleotide fragments, which when so combined, encode said polypeptide.

13. The method according to claim 12, wherein the oligodeoxynucleotide fragments are the 22 DNA fragments shown in FIG. 3.

14. A host organism transformed by DNA containing a synthetic gene for expression of human epidermal cell growth factor having the DNA sequence:

AACAGTGATTCAGAATGTCCTCTCTCACACGATGGAT
ACTGCCTCCATGACGGCGTGTGTATGTATATTGAAGC
ACTAGACAAATACGCATGCAACTGTGTAGTTGGCTAT
ATTGGTGAACGATGCCAGTACCGAGATCTGAAATGGT
GGGAACTGCGA.

15. The transformed host organism according to claim 14, wherein the DNA containing synthetic gene for expression of human epidermal cell growth factor is a recombinant DNA inserted into a plasmid vector.

16. The transformed host organism according to claim 15, which is a transformant *Escherichia coli* DH1/pTB 370.

17. The transformed host organism according to claim 15, which is a transformant *Escherichia coli* DH1/pTB 372, pRK 248 cIts.

18. The transformed host organism according to claim 15, which is a transformant mouse LA9-EGF-3 cell.

19. A method for producing human epidermal cell growth factor which comprises growing host organisms transformed by a synthetic DNA sequence which encodes and expresses the polypeptide, human epidermal cell growth factor, said DNA sequence being represented by:

AACAGTGATTCAGAATGTCCTCTCTCACACGATGGAT
ACTGCCTCCATGACGGCGTGTGTATGTATATTGAAGC
ACTAGACAAATACGCATGCAACTGTGTAGTTGGCTAT
ATTGGTGAACGATGCCAGTACCGAGATCTGAAATGGT
GGGAACTGCGA.

* * * * *